(12) United States Patent
Nerin et al.

(10) Patent No.: US 7,777,869 B2
(45) Date of Patent: Aug. 17, 2010

(54) DEVICE AND METHOD FOR MULTIPARAMETRIC ANALYSIS OF MICROSCOPIC ELEMENTS

(75) Inventors: Philippe Nerin, Nages et Solorgues (FR); Didier Lefevre, Saint Clement de Rivière (FR)

(73) Assignee: Horiba ABX SAS, Montpellier (FR)

( * ) Notice: Subject to any disclaimer, the term of this patent is extended or adjusted under 35 U.S.C. 154(b) by 27 days.

(21) Appl. No.: 11/912,055

(22) PCT Filed: Apr. 14, 2006

(86) PCT No.: PCT/FR2006/000819
§ 371 (c)(1),
(2), (4) Date: Apr. 25, 2008

(87) PCT Pub. No.: WO2006/111641
PCT Pub. Date: Oct. 26, 2006

(65) Prior Publication Data
US 2008/0283754 A1  Nov. 20, 2008

(30) Foreign Application Priority Data
Apr. 21, 2005  (FR) .................................. 05 04005

(51) Int. Cl.
*G01N 33/48* (2006.01)
(52) U.S. Cl. ........................................................ 356/39
(58) Field of Classification Search ...................... 356/39
See application file for complete search history.

(56) References Cited

U.S. PATENT DOCUMENTS

| | | | |
|---|---|---|---|
| 4,735,504 A * | 4/1988 | Tycko | 356/336 |
| 5,270,548 A | 12/1993 | Steinkamp | |
| 5,303,026 A * | 4/1994 | Strobl et al. | 356/318 |
| 5,986,271 A * | 11/1999 | Lazarev et al. | 250/458.1 |
| 2003/0205682 A1* | 11/2003 | Kapoor et al. | 250/458.1 |
| 2007/0096039 A1* | 5/2007 | Kapoor et al. | 250/458.1 |

FOREIGN PATENT DOCUMENTS

WO  92/08120  5/1992

OTHER PUBLICATIONS

Shapiro, Howard M. et al, "Combined Blood Cell Counting and Classification with Fluorochrome Stains and Flow Instrumentation", The Journal of Histochemistry and Cytochemistry, The Histochemical Society, Inc., vol. 24, No. 1, pp. 396-411, 1976.

* cited by examiner

*Primary Examiner*—Roy Punnoose
(74) *Attorney, Agent, or Firm*—Oblon, Spivak, McClelland, Maier & Neustadt, L.L.P.

(57) ABSTRACT

The invention concerns a device (DA) for analyzing microscopic elements, comprising firstly a measuring space (CM) for microscopic elements to be analyzed, secondly at least one source (S) delivering conjugated rays at the measuring space (CM), having at least two different analyzing wavelengths and designed to interact with the microscopic elements in the measuring space (CM) to form interacting rays, thirdly coding means (M) for encoding the rays upstream of the measuring space (CM) with different codes, fourthly optical filtering means (FO) for selectively filtering the interacting rays of fluorescence and/or diffusion depending on their wavelength, fifthly detecting means (DE, DF) for transforming into electric signals part at least of the interacting rays from the measuring space (CM), and sixthly analyzing means (MA) including decoding means (DRE, DRF) for decoding the electric signals to enable data representing the analyzed microscopic elements to be determined.

28 Claims, 5 Drawing Sheets

| Binary Table | | |
|---|---|---|
| 1 | 0 | 0 |
| 1 | 0 | 0 |
| 1 | 0 | 0 |
| 1 | 0 | 0 |
| 1 | 0 | 0 |
| 0 | 1 | 0 |
| 0 | 1 | 0 |
| 0 | 1 | 0 |
| 0 | 1 | 0 |
| 0 | 1 | 0 |
| 0 | 0 | 1 |
| 0 | 0 | 1 |
| 0 | 0 | 1 |
| 0 | 0 | 1 |
| 0 | 0 | 1 |

DEVICE AND METHOD FOR MULTIPARAMETRIC ANALYSIS OF MICROSCOPIC ELEMENTS

BACKGROUND OF THE INVENTION

The invention relates to the field of the analysis of microscopic elements, and more particularly to the devices dedicated to the characterization and to the counting of microscopic elements using a light.

Here, "microscopic elements" are understood to mean any element of microscopic dimensions, and notably biological particles or cells (prokaryotes and eukaryotes).

In the field of in vitro diagnostics (notably hematological counting or flow cytometry), it is conventional to use characterization and counting devices, based on the interaction between a light and the various microscopic elements that constitute a sample, in order to obtain qualitative and quantitative information on these microscopic elements.

Among the techniques that are widely used, those known as scattering techniques, which include transmission, diffraction, reflection and refraction, and those known as photoluminescence that include fluorescence and phosphorescence may notably be mentioned. They allow, separately or in combination, information on the shape, volume, size, color, density, structure, biochemical nature or particle size distribution to notably be obtained.

The characterizations of biological elements, and principally of blood cells, obtained with the common techniques of flow cytometry, are nevertheless based on a limited number of variables and of cellular discrimination possibilities.

Each measurement principle is a relatively simple physical method but the simultaneous multiplication of these measurements induces interactions that can interfere with the latter to the point of rendering them unusable. Thus, the implementation of multiple measurements is limited by the ability to avoid these interactions.

In the hematology analyzers and flow cytometers present on the market, the elements are generally detected either electronically by the method of impedance measurement known as the Wallace Coulter method, or by an optical method (scattering, photoluminescence).

For example, a volume and a refractive index can be deduced from the results of a scattering analysis based on a single wavelength and two different observation angles. This mode of detection is for example described in the patent U.S. Pat. No. 4,735,504 from the company TECHNICON Instruments Corp. The optical system described in this patent uses the measurements of light diffracted over two different ranges of angles, which allows the volume and refractive index values of the elements to be separated by a comparison of their optical responses with those of elements calibrated in volume and refractive index. The processing of these data values is based on the theory of light scattering by a spherical particle developed by Gustav MIE and notably described at the Internet address <http://en.wikipedia.org/wiki/Mie_scattering>.

In flow cytometry, it is commonly accepted that the measurement of the diffraction over a range of angles close to the optical axis (FSC (for "forward scatter") or on-axis diffraction) yields an indication of the volume of the microscopic elements analyzed. Furthermore, the light scattered orthogonally with respect to the optical axis (or "side scatter", or again, scattering at 90°) is described as being representative of the internal structure of the elements. These characteristics are closely linked to the angles and wavelengths at which the measurements are effected.

It is recalled that fluorescence is a phenomenon induced when an excitable molecule returns to the ground state after excitation by light energy at one of its characteristic wavelengths. The emission of fluorescence light always occurs at a frequency lower than that of excitation. The fluorescence emission is substantially isotropic. The measurement is generally effected away from the excitation axis of the incident light and through an optical filter transmitting to the detector only the spectral band of interest.

The molecular probes used in fluorescence can be vital or supravital dyes having an intrinsic affinity for a particular type of molecules. Intercalating dyes for nucleic acids such as orange thiazole, O-auramine, Y-pyronine or others may notably be mentioned, or immunological probes composed of an antibody onto which a dye marker, generally a single or tandem fluorochrome or sometimes a nano-crystal, is attached.

This mode of marking by the implementation of immunological probes has become widespread for cytological identification and notably according to the flow cytometry techniques previously described. The patent EP 0 022 670 from the company Ortho Diagnostics Inc. describes the identification of various cells using flow cytometry by their antigenic determinants. The technique described in this patent has opened the door to the very extensive development of immunophenotyping which is now recognized as a cellular identification technique that is efficient, safe and reliable.

Multiparameter cytological analysis may nevertheless be carried out without making use of antigenic identification. Thus, in the document "Combined Blood Cell Counting and Classification with Fluorochrome Stains and Flow Instrumentation" J. of Histochem. & Cytochem Vol 24. No. 1, pp. 396-411, 1976, Howard M. Shapiro has described a general classification of blood cells by means of a multiparameter cytometer performing absorption, diffraction and fluorescence measurements, and in which the elements are brought into contact with a mixture of specific fluorescent dyes of nucleic acids and of proteins.

In parallel, the multiplication of the fluorescence measurement wavelengths in the analyzers has allowed the use of a growing number of markers and hence of antibodies, as indicated in the document by John A. Steinkamp, "A Modular Detector for Flow Cytometric Multicolor Fluorescence Measurements", 1987, Cytometry 8: pp. 353-365, but has also very seriously increased the complexity of the devices and their implementation.

The combined use of dyes excited by a single wavelength quickly presents limitations owing to the regions of spectral overlap of their excitations and/or of their fluorescence emissions.

In order to overcome these problems of spectral overlap, use is generally made of a correction method called "compensation" which globally consists in reducing the fluorescence signal of the microscopic element analyzed by the proportional part of spectral overlap of other microscopic elements, as indicated in the document "Spectral Compensation for Flow Cytometry: Visualization Artifacts, Limitations and Caveats", Mario Roederer 2001, Cytometry 45, pp. 194-205.

One problem induced by the compensations resides in the fact that they are calculated in average value and that, for a given family of fluorochromes, it is not possible to fix their values once and for all. Indeed, there exist wide variations in the physical properties of the fluorochromes of the same family notably depending on the origin of the supply. The same product coming from different manufacturers can thus lead to different sets of compensations. This especially poses a problem in the field of diagnostics because uncontrolled sources of supply could lead to erroneous and therefore potentially dangerous measurements. For example, the efficiency of the PE-TR transfer and the nature of the antibody employed are not sufficiently stable in order to accept a definitive software compensation as is notably explained in the article by Carleton C. Steward and Sigrid J. Stewart "Four color compensation", Cytometry, Vol. 38, pp. 161-175, 1999.

The use of several excitation wavelengths allows a wider choice of dyes to be opened up and allows the emission spectra to be separated more easily. The various excitation wavelengths are frequently spatially separated in the measurement tank offering in this case the advantage of several independent measurements as described in the article by J. Steinkamp "Improved multilaser/multiparameter flow cytometer for analysis and sorting of cells and particles" John A. Steinkamp, Robert C. Habbersett, and Richard D. Hiebert; Review of Scientific Instruments Vol 62(11) pp. 2751-2764, November 1991. The problem with this method resides in the fact that the spatial displacement induces a temporal phaseshift in the responses and that the re-adjustment of the information must be done downstream, either by delaying the information in an analog fashion, or by re-adjusting the measurements by software means.

The multiplication of the excitation wavelengths (notably of the laser sources), together with measurements of fluorescence and of other optical parameters, leads to technological complexity and a significant difficulty in implementation as is for example described in the article entitled "Nine Color Eleven Parameter Immunophenotyping Using Three Laser Flow Cytometry", Martin Bigos 1999, Cytometry 36, pp. 36-45.

The level of risk of error in the interpretation of the results increases with the number of parameters and the use of these instruments is reserved for very specialized technicians at the risk of obtaining results that are inappropriate and false, and therefore potentially dangerous.

One limitation of the compensations, whose level of criticality increases with the number of fluorochromes, relates to the propagation and the amplification of the noise in the fluorescence measurements and of their linear combinations which are used to correct the raw measurements.

Since no known analyzing device is entirely satisfactory, the object of the invention is therefore to improve the situation. In particular, the invention is designed to overcome the problems of compensation generally encountered in the prior art.

SUMMARY OF THE INVENTION

For this purpose, the invention provides a device for analyzing microscopic elements, comprising:
firstly, a measurement space for microscopic elements to be analyzed,
secondly, at least one source delivering radiation having at least two different analyzing wavelengths and designed to interact with the microscopic elements within the measurement space in order to form interaction radiation,
thirdly, detection means responsible for transforming at least a part of the interaction radiation originating from the measurement space into electrical signals, and
fourthly, analysis means responsible for analyzing the electrical signals so as to allow data representative of the analyzed microscopic elements to be determined.

Here, "interaction radiation" refers to radiation coming from the interaction between the analyzing beam and the microscopic elements analyzed. This interaction radiation can notably be radiation from scattering (refraction, reflection, diffraction) and/or photoluminescence (fluorescence, phosphorescence).

Furthermore, here, "radiation" is understood to mean a light beam of wavelength in the range between ultraviolet and infrared, in other words between around 100 nm (0.1 μm) and around 5000 nm (5 μm).

The device according to the invention is characterized:
in that its coded radiation is conjugated within the measurement space,
in that it comprises i) coding means responsible for encoding the radiation upstream of the measurement space with different codes, and ii) optical filtering means responsible for selectively filtering the fluorescence and/or scattering interaction radiation as a function of its wavelength, upstream of the detection means, and
in that its analysis means comprise decoding means responsible for decoding the electrical signals so that they are analyzed as a function of their code of origin.

Here, "coding" refers to the action of applying a code ($\omega i$) to an analyzing radiation beam (Ri) before its interaction with the microscopic elements, with a view to generating the interaction radiation which itself comprises the code of origin. In particular, the codes ($\omega i$) may be chosen in such a manner as to apply a pulsed modulation to each analyzing radiation beam.

These pulses can be synchronous or asynchronous. In the case of synchronous pulses, all the wavelengths interact simultaneously with the microscopic elements analyzed. In the case of asynchronous pulses, the wavelengths interact sequentially with the microscopic elements to be analyzed. The optical filtering means are designed, for a given family of fluorochromes and for a given type of coding, in such a manner as to avoid compensations being carried out.

The device according to the invention can comprise complementary characteristics which may be taken separately or in combination, and notably:
its optical filtering means can be responsible for selectively filtering the fluorescence interaction radiation whose wavelengths belong to fluorescence analysis bands respectively inserted between two analyzing wavelengths and placed beyond the longest analyzing wavelength;
its coding means can be responsible for coding the analyzing radiation periodically and/or sinusoidally in intensity;
at least a part of its coding means can act on the source upstream of a distribution output for the radiation—this part can be integrated into the source;
at least a part of its coding means can act on the radiation downstream of the source so as to form the analyzing radiation;
its coding means can modulate in intensity the radiation delivered by the source, for example by means of an acoustooptic modulator, so as to form the analyzing radiation;
the source can comprise at least two coupled lasers, of the monochrome type if desired, and/or at least one lightemitting diode, whose analyzing radiation is conjugated within the measurement space. As a variant, the source can comprise a source of substantially continuous polychromatic light, such as for example a polychromatic laser, an incandescent lamp or an arc lamp;
the source can deliver the analyzing radiation according to a continuous mode and/or a pulsed mode;

the intensity of each analyzing radiation beam delivered by the source can be adjustable;

its detection means can comprise a multiplicity of photosensitive sensors dedicated to the detection of interaction radiation (representative of scattering and of fluorescence process(es)) induced by the analyzing radiation on the microscopic elements to be analyzed. As a variant, the detection means can comprise a multiplicity of photosensitive sensors dedicated to the detection of interaction radiation representative of scattering process(es) and implanted in a location defined by an axis intercepting the general direction of propagation of the analyzing radiation within the measurement space, this axis being oriented at an angle in the range from 0° to 360° with respect to the general direction;

its analysis means can allow the refractive index of one type of microscopic elements analyzed to be deduced from the signals resulting from the transformation of the interaction radiation representative of a scattering process. In particular, when the microscopic elements belong to a sample of blood, the analysis means can notably allow the intra-erythrocytic hemoglobin content or the intracytoplasmic protein content of the leucocytes to be determined;

its analysis means can allow a degree of coupling representative of the transfer of energy between two light-emitting agents (or fluorochromes) having different wavelengths to be deduced from the signals resulting from the interaction between the analyzing radiation and the two light-emitting agents.

The invention also provides a method for analyzing microscopic elements, comprising:

a first step in which microscopic elements placed within a measurement space are illuminated by means of analyzing radiation conjugated within the measurement space and having at least two different analyzing wavelengths and codings according to different chosen codes, in such a manner as to form interaction radiation, a second step in which at least a part of the interaction radiation is collected, and then separated and filtered as a function of its wavelength, a third step in which the filtered interaction radiation is detected, and then transformed into electrical signals, and a fourth step in which the detected signals are decoded as a function of their code of origin in such a manner as to allow data representative of the analyzed microscopic elements to be determined.

The method according to the invention can comprise complementary characteristics that can be taken separately or in combination, and notably:

in the first step, the analyzing radiation can be applied sequentially or simultaneously to the microscopic elements to be analyzed;

in the first step, a sinusoidal modulation can also be applied to the intensity of the analyzing radiation;

in the second step, the fluorescence interaction radiation, whose wavelengths belong to fluorescence analysis bands respectively inserted between two analyzing wavelengths and placed beyond the longest analyzing wavelength, can be selectively filtered;

in the fourth step, the refractive index of one type of microscopic elements analyzed can be deduced from the signals resulting from the transformation of the interaction radiation representative of a scattering process. In particular, when the microscopic elements belong to a sample of blood, the intra-erythrocytic hemoglobin content or the intracytoplasmic protein content of the leucocytes can notably be determined;

in the fourth step, a degree of coupling representative of the transfer of energy between two light-emitting agents (fluorochromes) having different wavelengths can be deduced from signals resulting from the interaction between the analyzing radiation and the two light-emitting agents.

The invention is particularly well suited, although in a non-limiting manner, to the field of in vitro diagnostics (notably flow cytometry), and to the analysis of any microscopic element in a fluid. It is notably applicable to biological, biochemical, chemical, particulate, morphological analysis and, in particular, to multiparameter flow cytometry, the analysis of charged particles in a liquid or gaseous fluid, and particle size distribution.

BRIEF DESCRIPTION OF THE DRAWINGS

Other characteristics and advantages of the invention will become apparent upon examining the detailed description hereinbelow and the appended drawings, in which.

DETAILED DESCRIPTION OF THE INVENTION

The appended drawings will be able to be used not only to complete the invention, but also to contribute to its definition, where necessary.

Figure 1A:
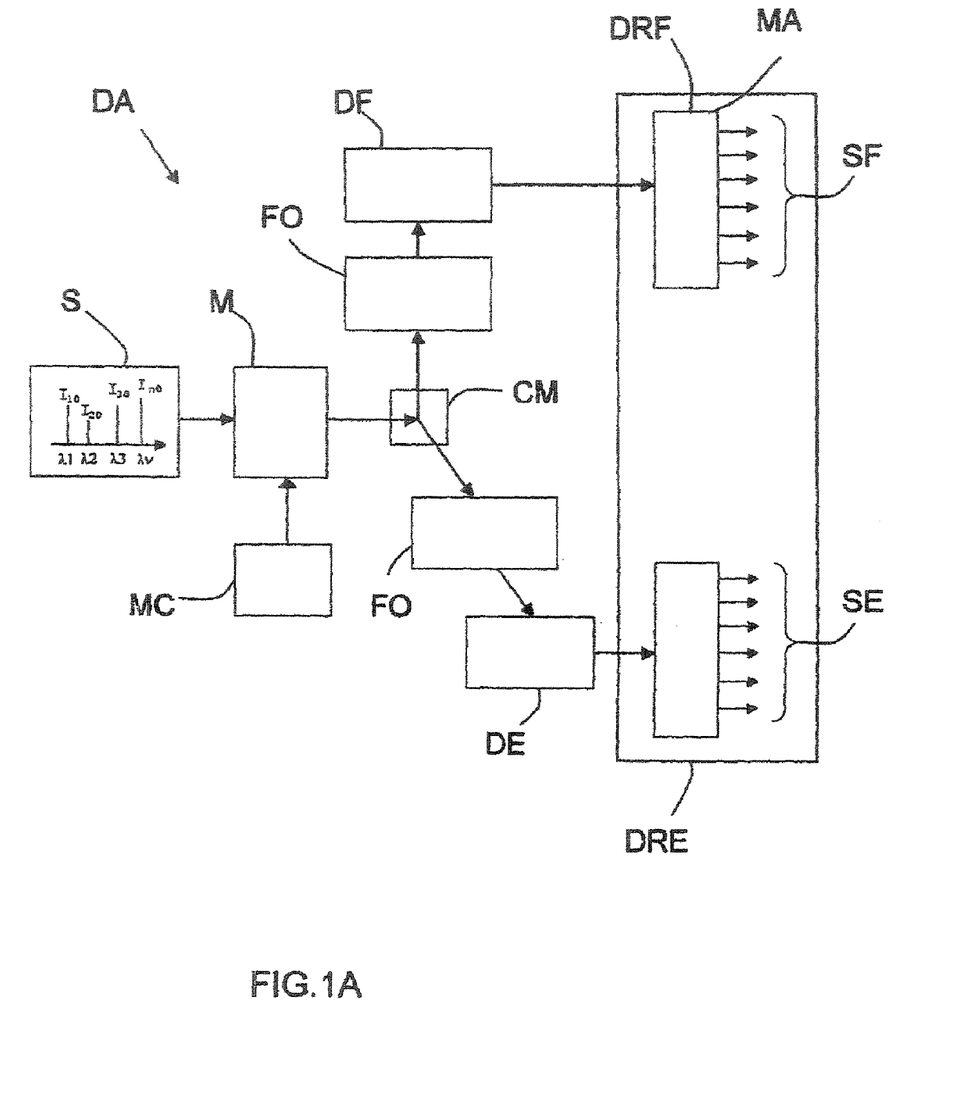
FIG. 1A illustrates schematically and functionally a first exemplary embodiment of an optical analyzing device according to the invention.
Figure 1B:
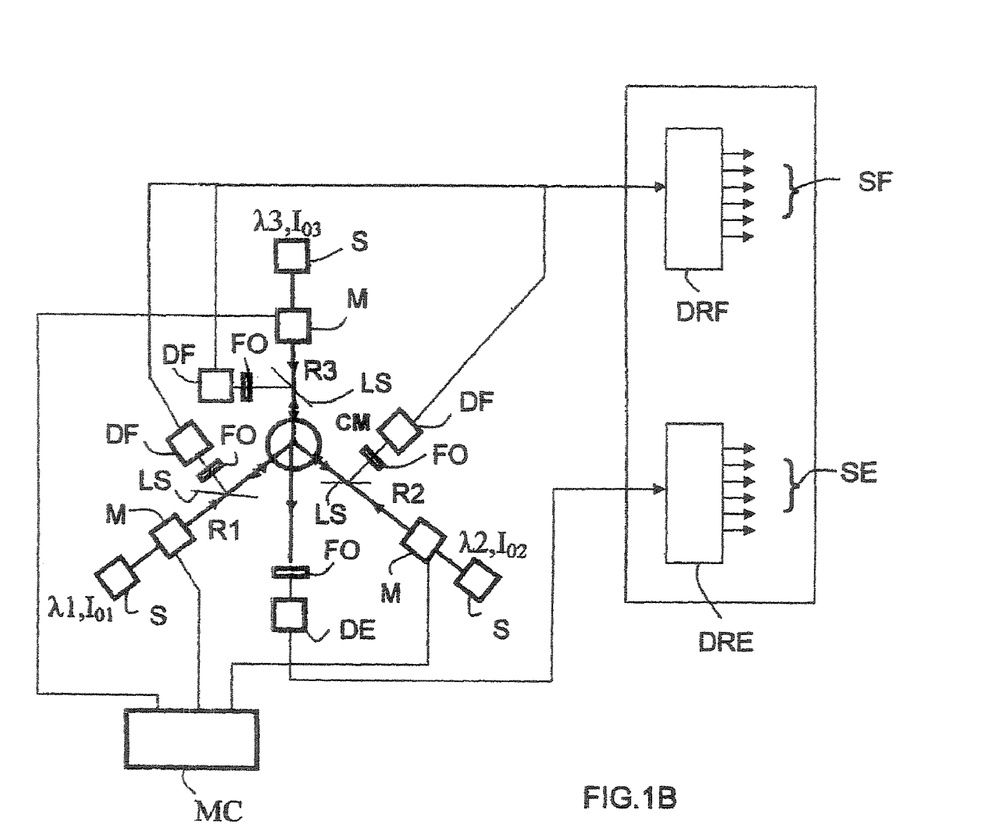
FIG. 1B illustrates schematically and functionally a second exemplary embodiment of an optical analyzing device according to the invention in which several sources are capable of generating radiation that is intended to be conjugated within the measurement space (CM)

Reference is first of all made to FIGS. 1A and 1B in order to describe two exemplary embodiments of optical analyzing device DA, according to the invention.

In the following, it is considered that the device DA is dedicated to the characterization and counting in flow cytometry of the microscopic elements in a sample of blood. However, the invention is not limited to either this type of sample or to flow cytometry. It actually relates to any type of sample comprising microscopic elements to be analyzed optically by fluorescence and/or by light scattering, and notably particles in a fluid or biological samples.

Figure 2A:
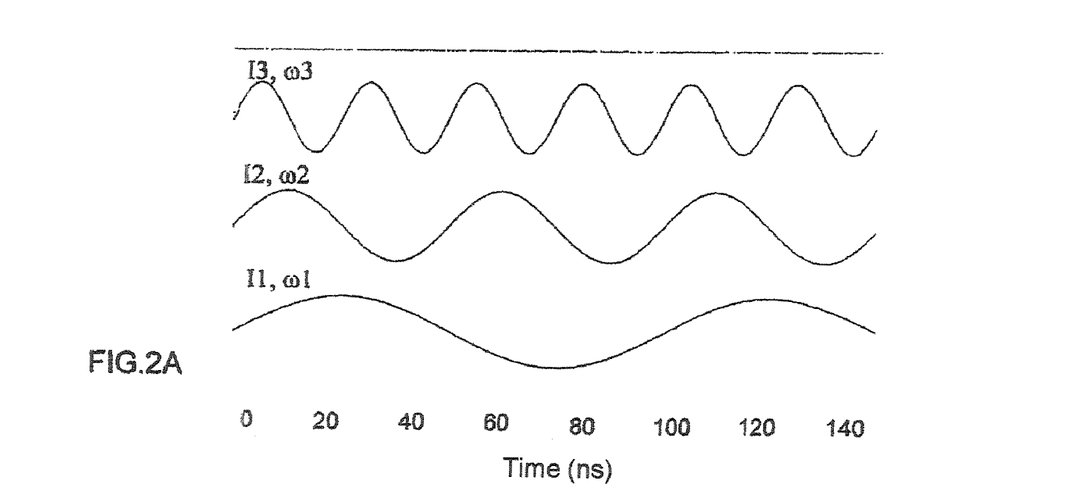
FIG. 2A illustrates an example of sinusoidal coding, with simultaneous illumination, that may be applied to the light radiation.
Figure 2B:
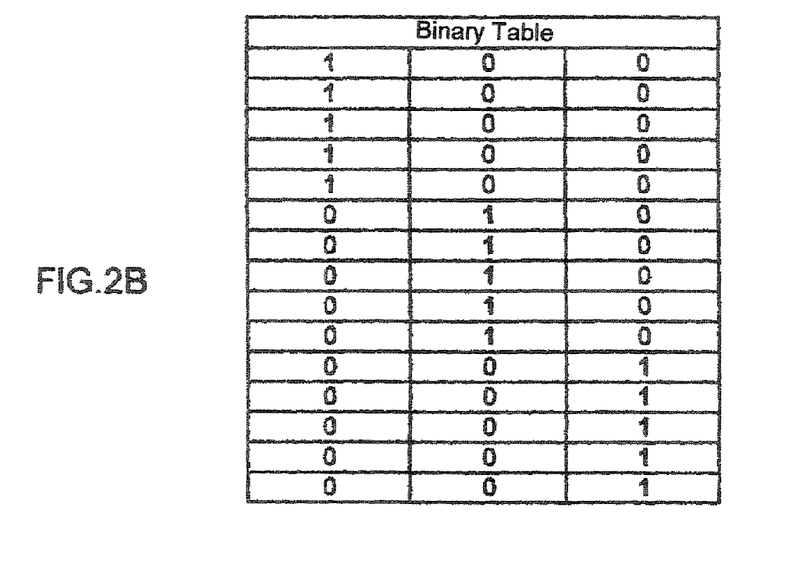
FIG. 2B illustrates an example of sequential binary coding.
Figure 2C:
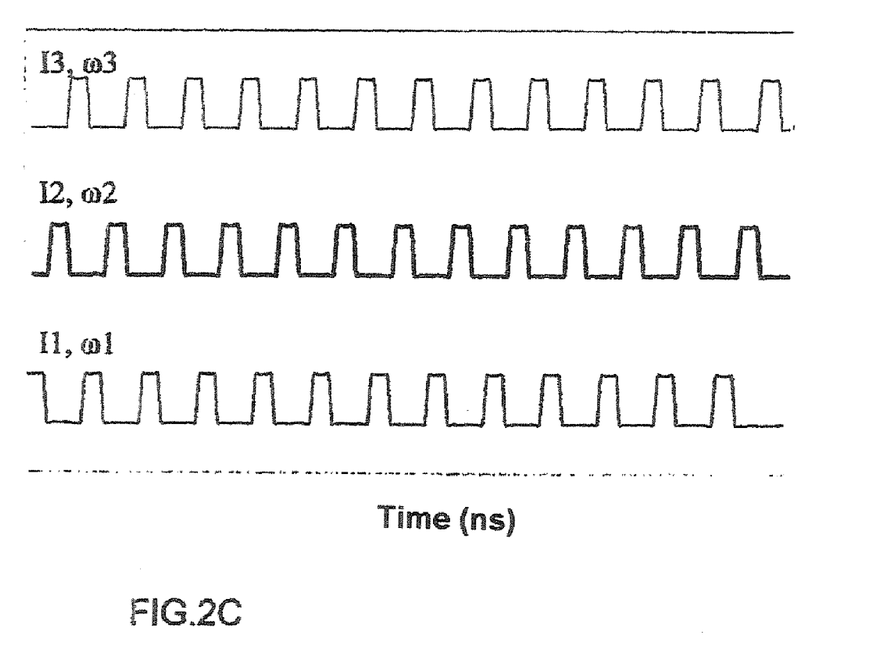
FIG. 2C shows the forms of the signals with the binary coding in FIG. 2B, repeated periodically.

As is schematically and functionally illustrated in FIGS. 1A and 1B, an analyzing device DA, according to the invention, comprises at least:

one measurement space CM, sometimes called measurement tank (or measurement region, or even measurement window) within which are located (or through which pass) the microscopic elements of the sample to be analyzed, one (or several) source(s) S responsible for delivering radiation Ri having at least two different analyzing wavelengths λ1 to λn, conjugated within the measurement space (CM), [in the case of FIG. 1A, a single source S is used to deliver several wavelengths, whereas in the case of FIG. 1B, three sources S are used to each deliver one wavelength—by definition, it is considered here that the different sources in FIG. 1B form sub-parts of a radiation source]

coding means M responsible at least for coding (modulating) each light radiation beam Ri of wavelength λi with a specific code ωi (here i=1 to n, for example n=2 or 3), and possibly controlled by a control module MC, the coding being for example of the type of that shown in FIGS. 2A to 2C, optical filtering means FO responsible for selectively filtering the interaction radiation coming from the measurement space CM, after having potentially interacted with the microscopic elements, and whose wavelengths preferably belong to fluorescence analysis bands Bi which are each inserted between two analyzing wavelengths λi and λi+1, with the exception of the last one (that has the longest wavelengths) which is placed beyond the analyzing wavelength λn, which is the longest, detection means DF and/or DE comprising photosensitive sensors (or photosensors) responsible for transforming into electrical signals at least a part of the fluorescence and/or scattering interaction radiation coming from the measurement space after having potentially interacted with the microscopic elements, and analysis means MA comprising at least decoding means DRF and/or DRE responsible for decoding the electrical signals that are transmitted to it by the detection means DF and/or DE, in order for them to be analyzed as a function of their code ωi in such a manner as to allow data representative of the microscopic elements analyzed to be determined.

It is important to note that the analyzing device DA can carry out fluorescence and/or scattering analyses. Consequently, depending on the variant, it possesses:

either optical filtering means FO, associated with the detection means dedicated to the fluorescence DF with the associated decoding means DRF, but no detection means dedicated to the scattering DE and the associated decoding means DRE, or optical filtering means FO, associated with the detection means dedicated to the fluorescence DF with the associated decoding means DRF, and optical filtering means FO, associated with the detection means dedicated to the scattering DE and the associated decoding means DRE, or else detection means dedicated to the scattering DE and the associated decoding means DRE but no optical filtering means FO nor detection means dedicated to the fluorescence DF with the associated decoding means DRF.

When the analyzing device DA is dedicated to the flow cytometry or to the counting, its measurement tank CM (or measurement space) can be of the type referred to as "with flux coupling", such as that described in the patent document FR 2653885.

In the example in FIG. 1A, the source S is responsible for generating a single light beam composed of the superposition of n radiation beams Ri of respective wavelengths λ1 to λn, with n≧2. In the example in FIG. 1B, each of the three sources S is responsible for generating a single light beam composed of one radiation beam Ri (R1, R2 or R3) of wavelength λi (λ1, λ2 or λ3).

The intensity of each beam, denoted $I_i$, can be adjusted to a predetermined value. This for example allows the fluorescence intensity of a family of fluorochromes (or fluorescent compounds) to be placed at a predetermined level when excited by the analyzing radiation Ri of wavelength λi and of intensity $I_i$. A family of fluorochromes for which the quantum fluorescence efficiency is very high (which is for example the case for certain molecular probes such as orange thiazole) can also be excited with a low intensity. In contrast, when fluorochromes with identical quantum efficiencies are used simultaneously for marking antigens expressed differently on the same cell, the fluorescence levels emitted by the various fluorochromes can be approximately equalized by acting on the intensities of their respective analyzing radiation beams.

Owing to this possibility for controlling the fluorescence levels of the microscopic elements, the source S is also called an optical "synthesizer-equalizer".

Each of the n radiation beams Ri of intensity $I_i$ can also be coded in intensity periodically and/or sinusoidally by coding means which are discussed hereinbelow. This coding process, which is for example of the type of that illustrated in FIGS. 2A to 2C, is determinant because it allows, thanks to the decoding means DRF and/or DRE, the demultiplexing of the radiation resulting from the interaction with the microscopic elements analyzed (notably by the mechanisms of fluorescence and/or scattering).

When the source S comprises lasers, such as for example semiconductor lasers, or light-emitting diodes, the coding can be achieved by acting on the injection current, the modulator M then being an electrical generator capable of delivering image electric currents of the codes applied to each of the radiation beams. When the coding is of the sinusoidal type, the coding consists notably in fixing modulation frequencies ωi which are functions of various experimental considerations that will be explained hereinbelow.

At the output of the modulator M there are n radiation beams Ri of chosen wavelengths λi and of intensity $I_i$, potentially chosen and conjugated in the measurement space. In the case of a sinusoidal coding, the expression for the light intensity $I_i$ (in W/m$^2$) is given by equation A1 in the Appendix.

The beam or beams of n radiation Ri is (are) focused by optical means not shown inside the measurement (or counting) space where they interact with the microscopic element (here a biological cell) previously marked and/or dyed according to any technique known to those skilled in the art.

Figure 3:
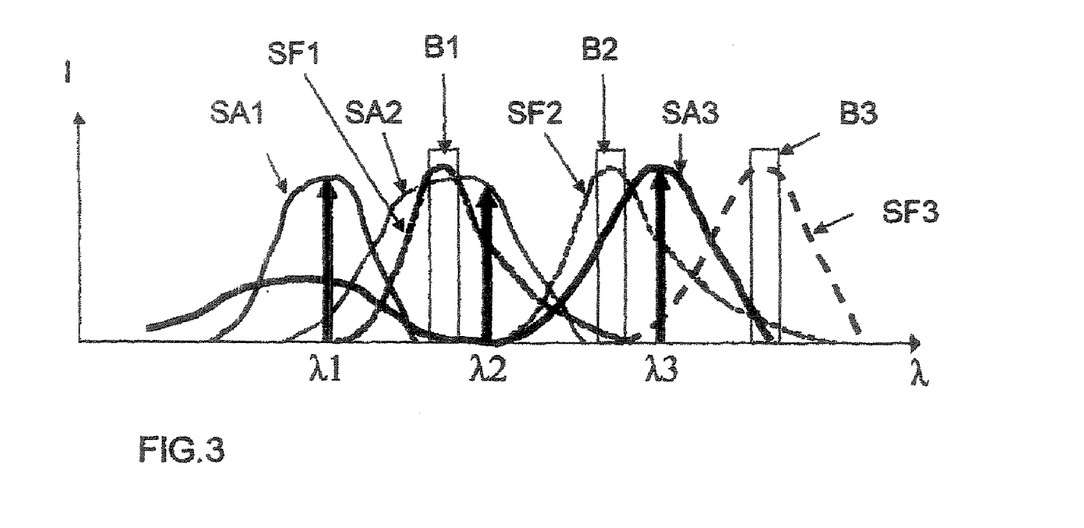
FIG. 3 is a diagram illustrating three absorption spectra of fluorochromes (SA1 to SA3) corresponding to three analyzing wavelengths ($\lambda 1$ to $\lambda 3$), and three fluorescence spectra of these same fluorochromes (SF1 to SF3)

In FIG. 3 are shown three absorption spectra SA1 to SA3 of three fictitious fluorochromes corresponding to three analyzing wavelengths λ1 to λ3, and the three fluorescence spectra SF1 to SF3 of these same three fluorochromes which are detected by the fluorescence detection means DF. The references B1 to B3 denote the three wavelength bands that the optical filtering means FO let through.

The number of fluorochromes of different types here is limited to three in order to facilitate the description. However, the invention is not limited to this number. It can actually apply to any given number of fluorochromes.

According to the invention and as can be observed in FIG. 3, the band B1, which corresponds to the maximum of the fluorescence spectrum SF1 of the first fluorochrome, is inserted between the analyzing wavelengths $\lambda 1$ and $\lambda 2$, the band B2, which corresponds to the maximum of the fluorescence spectrum SF2 of the second fluorochrome, is inserted between the analyzing wavelengths $\lambda 2$ and $\lambda 3$, and the band B3, which corresponds to the maximum of the fluorescence spectrum SF3 of the third fluorochrome, is placed beyond the analyzing wavelength $\lambda 3$ (which is the longest of the three).

Preferably, to each band Bi, there corresponds a fluorescence detector DFi.

The analysis of the absorption SAi and fluorescence SFi spectra allows a matrix equation to be written between the (photoelectric) signals delivered by the (n=3) detectors and the quantities of fluorochromes: $[PMo]=I_1[C][Q]+I_2[D][Q]+I_3[E][Q]$.

Here, [PMo] is the matrix of the photoelectric signals delivered by the (n=3) fluorescence detectors DFi, the index o indicating a fluorescence signal in the absence of energy transfer. [C], [D] and [E] here are the transfer matrices allowing the fluorescence light beams to be calculated. [Q] here is the matrix of the quantities Q1 to Q3 of the (n=3) fluorochromes, expressed as number of moles.

The coefficients $c_{ij}$, $d_{ij}$ and $e_{ij}$ of the transfer matrices [C], [D] and [E] are respectively given by equations A2, A3 and A4 in the Appendix.

The examination of the decomposition of the matrix [PMo] and of the associated coefficients shows that it is possible to determine each molar concentration Qi without linear combination of the measurement signals. With the aforementioned writing conventions, the molar concentrations Qi are given by equations A5 to A7 in the Appendix. In these three equations A5 to A7, the terms $PMi(\omega i)$ represent a characteristic of code $\omega i$.

This characteristic can for example be the peak amplitude or even the r.m.s. value of the signal over an interval of time limited by the duration of the analyzing light pulse or, alternatively, a temporal characteristic of the signal such as the fade time of a fluorescence light. The direct determination of the molar concentrations Qi of the fluorochromes, without using a linear combination of the measurements, increases the precision of the results and therefore the precision of the diagnosis.

The use of compensations (of linear combination of various signals) is therefore avoided in order to determine the molar concentration of a given fluorochrome. The robustness of the invention allows the interference effects, hence the compensations, to be avoided and is therefore more reliable and more robust than the conventional methods used up to now.

The invention can also allow the degree of coupling between two fluorochromes (or fluorescent compounds) to be determined which corresponds to the transfer of energy (by fluorescence) between a "donor" fluorochrome and a "receiver" fluorochrome. This determination of the coupling between two fluorochromes can for example allow the distance between epitopes or else their physical association to be measured.

In view of the writing conventions given hereinabove, the expressions for the various fluorescence signals in the presence of an energy transfer are given by equations A8 to A10 in the Appendix.

The case of the transfer of energy between the first two fluorochromes will be described analytically hereinbelow. In this case, the expressions for the various photoelectric signals given by equations A8 to A10 in the Appendix can be rewritten in the form of equations A11 to A13 in the Appendix. This results from the fact that only the coefficients $\kappa_{12}$ and $\rho_{12}$ need to be taken into account, the other coefficients $\kappa_{ij}$ and $\rho_{ij}$ being taken equal to 1.

In view of the expressions for equations A2 to A7, from the equations A11 and A12 in the Appendix, the three equations A14 to A16 in the Appendix may then be extracted. Then, by eliminating from the equations A14 to A16 the molar concentrations Q1 to Q3, the energy transfer parameter $\kappa_{12}$ between the first two fluorochromes can be determined. The formula for this energy transfer parameter $\kappa_{12}$ is given by equation A17 in the Appendix.

The molar concentration Q1 in the presence of a transfer of energy between the first two fluorochromes can then be reformulated as indicated by equation A18 in the Appendix. The molar concentrations Q2 and Q3 in the presence of a transfer of energy between the first two fluorochromes are then given by equations A6 and A7 in the Appendix.

It is important to note that the equations given hereinabove and in the Appendix can be extended in the case where a transfer of energy between the first and third fluorochromes and/or between the second and third fluorochromes is also taken into account.

Figure 4:
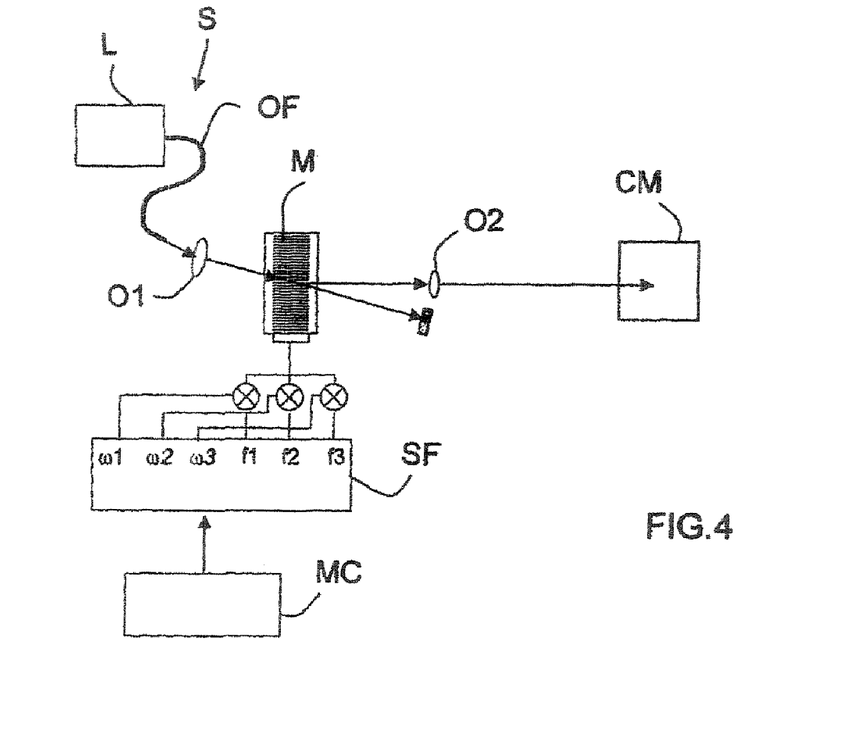
FIG. 4 illustrates schematically an exemplary embodiment of the part of the analyzing device situated upstream of the measurement tank, in which the modulator is of the acoustooptic type.

In FIG. 4, an upstream part of an analyzing device DA according to the invention is shown, in which the source S supplies broadband light (radiation) to a modulator M that provides both the selection of the analyzing wavelengths and the coding in intensity of the corresponding radiation. Here, broadband light (or white light, or polychromatic light) is obtained by means of a pulsed laser L injected into a microstructured optical fiber OF. This type of source S is for example described by the applicant in the article entitled "White-light supercontinuum generation in normally dispersive optical fiber using original multi-wavelength pumping system", Optics Express, vol. 12, No. 19, September 2004.

The laser L serving as pump for the microstructured optical fiber OF may for example be replaced by a neodynium-doped or ytterbium-doped fiber optic laser operating in a regime of reverse-biased modes (for example with a pulse-repetition rate of 50 MHz), followed by an optical amplifier capable of delivering a flux compatible with an excitation in a nonlinear interaction regime of the microstructured optical fiber OF.

The polychromatic light that is delivered by this type of source S differs from that delivered by an incandescent lamp in the fact that its spatial coherence is extremely high (all the photons of the continuum are emitted in the same spatial mode).

Of course, other types of source S may be envisioned. Thus, the source can comprise at least two coupled lasers, possibly of the monochrome type, and/or at least one light-emitting diode. It may also comprise other types of substantially continuous polychromatic light source, such as for example an incandescent lamp or an arc lamp.

The beam of light coming from the microstructured optical fiber OF is conditioned by means of a focusing optical system O1, with corrected chromatism or zero chromatism thanks, for example, to an optical combination of the catadioptric type (mirrors). This light beam is focused onto the modulator M, which takes the form of an acoustooptic cell whose angular chromatism is preferably corrected by spatial superposition of diffraction gratings of pitch adapted to the diffraction at the Bragg angle of incidence.

These diffraction gratings are created by the superposition of acoustic waves sustained by a vibrating element of the piezoelectric type powered by an electrical signal capable of sustaining n modulation signals $m_i(t)=M_i \cos 2\pi\omega_i t$ which are involved in the equation A1 in the Appendix giving the modulated intensity $I_i(t)$.

Such an acoustooptic modulator M is for example that which is marketed by the company A-A Opto-Electronic.

Here, the acoustooptic modulator M is controlled by means of control electronics SF capable of simultaneously generating (at least) 3 acoustic frequencies (f1, f2, f3), and itself controlled by the control module MC (which can form part of a computer system comprising a control software interface). The band of acoustic frequencies is for example in the range between 80 MHz and 150 MHz. The frequencies are chosen in such a manner as to allow the selection, within the light continuum of the beam, of three (in the example described) quasi-monochromatic radiation beams, for example of wavelengths equal to 488 nm (blue), 570 nm (yellow) and 976 nm (infrared). The equalization of the three radiation beams is obtained by acting on the intensity of the acoustic signal. The higher the acoustic intensity, the higher the diffraction efficiency within the acoustooptic modulator M. In other words, the quantity of light that can go from the 0 diffraction order to the +1 diffraction order can be regulated (by acting on the intensity of the acoustic signal).

Quasi-monochromatic radiation here is understood to mean light emitted in a spectral band in the range between 1 and 50 nm in width.

It is important to note that all of the parameters of the source S and of the modulator M can be remotely adjustable by means of the control module MC (for example of computer type). Thus, by means of a software interface, all the parameters of the source S, such as the various analyzing wavelengths and the respective intensities of the analyzing radiation and others, can be chosen by the operator.

The analyzing radiation Ri, delivered at the output of the modulator M, is for example conditioned by an optical system O2 so as to be focused within the measurement tank (or space) CM.

The modulation frequencies $\omega i$ are chosen as a function of various parameters, such as for example the speed of passage of the biological cell through the measurement space CM, the dilution, the size of the optical window of the measurement space CM, the bandwidth of the acquisition part (optical filtering means FO, detectors DE and/or DF) of the analyzing device DA.

For example, if the biological cell to be analyzed passes through an analyzing beam of radiation having a Gaussian profile, of width at half-height of around 30 μm, at a speed of around 1 m/s, it will generate a pulse of interaction radiation (fluorescence or scattering (extinction)) of substantially Gaussian shape and of duration substantially equal to 30 μs. The frequency spectrum is then of Gaussian shape and its height at half-height is substantially equal to 0.3/30 μs, or around 10 kHz. In order to avoid electronic crosstalk phenomena, it is preferable to choose a minimum separation of 100 kHz between two consecutive modulation frequencies $\omega i$ and $\omega i+1$. For example, $\omega 1$ can be chosen equal to 100 kHz, $\omega 2$ equal to 200 kHz and $\omega 3$ equal to 300 kHz.

If the flow-through duration is around 5 μs instead of 30 μs, each interaction radiation pulse occupies a frequency band of around 200 kHz and therefore the modulation frequencies must be separated by at least this characteristic frequency: for example, $\omega 1=1$ MHz and $\omega 2=1.5$ MHz.

It is important to note that other types of modulator M may be envisioned. Notably, the modulator M may, at least in part, be integrated into the source S or else, at least, in part, be downstream of the latter. The modulator M may also be placed, at least in part, upstream of the source M, for example in such a manner as to control its power supply current.

The part of the analyzing device DA situated upstream of the measurement tank CM and described hereinabove with reference to FIG. 4 can be coupled to a downstream part of the type of that illustrated in FIG. 1A or 1B. In this case, a part of the interaction radiation resulting from the scattering arrives at the detector DE where it is converted into electrical signals processed by the analysis module MA.

In FIG. 1A, the detector DE is, by way of example, oriented in a mean direction of around 45° to the general direction of propagation of the analyzing radiation within the measurement space CM. However, the angle of this mean direction can take any given value in the range from 0° to 360° depending on the type of information desired.

The detector DE transmits these photoelectric signals to the decoder (or demodulator) DRE of the analysis module MA, in order for it to decode them. This demodulator DRE is for example configured in the form of filtering (decoding) stages, for example of the analog type. As a variant, the photoelectric signals could be digitized and the filtering (decoding) operation could be carried out digitally, in real time or by post-processing (after recording).

At the output of the demodulator DRE, there are three scattering signals SE($\lambda 1=488$ nm), SE($\lambda 2=570$ nm) and SE($\lambda 3=976$ nm). The values of the scattering signals SE(488 nm) and SE(976 nm) allow the scattering cross sections $C_{ext}$ (488 nm) and $C_{ext}$(976 nm) to be determined which are needed for the determination of the refractive indices and of the volumes of the red blood cells.

The conversion of the scattering signals into cross sections is for example achieved by a calibration procedure using microbeads calibrated in refractive index and volume. These microbeads can for example be made of latex or come from emulsions.

The part of the interaction radiation resulting from the fluorescence passes through a signal conditioning optical array before arriving at the optical filtering means FO. The interaction radiation is then filtered into wavelengths so that only that whose wavelengths belong to the n (here n=3) detection bands Bi is conserved.

In FIG. 1A, the fluorescence detection means DF are all grouped in the same location. In this case, optical filtering means FO form a multi-band filter.

Figure 5:
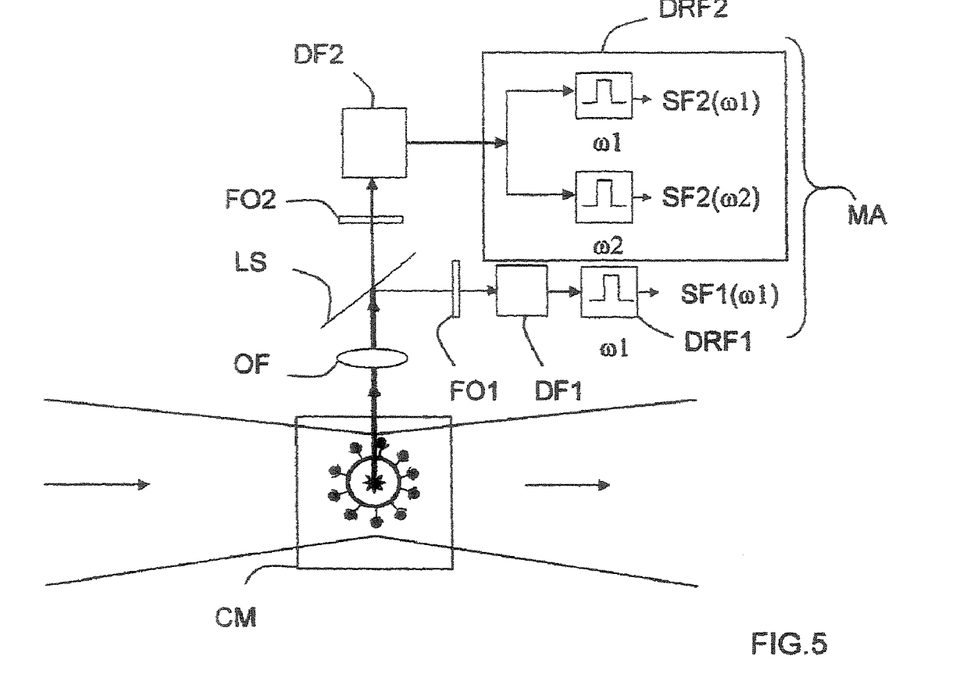
FIG. 5 illustrates schematically an exemplary embodiment of the part of the analyzing device situated downstream of the measurement tank and dedicated to the detection and the analysis of the fluorescence.

As illustrated in FIG. 5, separation means LS can be used in order to spectrally separate the fluorescence interaction radiation into at least two parts. For this purpose, a separator plate LS, possibly of the dichroic type, can for example be used. Thus, (at least) two fluorescence detection and analysis channels are defined, allowing the fluorescence signals from a first type of fluorescent fluorochromes to be obtained on one channel in the first optical filtering band B1 of the optical filter FO1, and on a second channel, the fluorescence signals from a second type of fluorescent fluorochromes in the second optical filtering band B2 of the optical filter FO2.

The device in FIG. 5 can for example be used for the quantification of nucleic acids (RNA+DNA) and the detection of a membrane antigen.

Here, two analyzing radiation beams R1($\omega 1$) and R2($\omega 2$), having wavelengths $\lambda 1$ and $\lambda 2$ respectively equal to 488 nm and 560 nm, are used in order to detect the fluorescences of the two fluorochromes (orange thiazole and PE) allowing the nucleic acids and the membrane antigen of the leucocytes to be respectively marked. The two radiation beams R1($\omega 1$) and R2($\omega 2$) are obtained by means of the device previously described with reference to FIG. 4.

The first detection band B1 is centered on λ3 (530 nm) and has for example a spectral width of 30 nm, whereas the second detection band B2 is centered on λ4 (670 nm) and has for example a spectral width of 40 nm. In accordance with the invention, λ3 is in the range between λ1 and λ2, and λ4 is greater than 2.

The interaction radiation filtered by the first optical filter FO1 arrives at a first fluorescence detector DF1 where it is converted by photodetectors into electrical signals transmitted to a first fluorescence decoder (or demodulator) DRF1 of the analysis module MA that is responsible for demodulating them according to the first modulation frequency ω1 in order to deliver the signal PM1(ω1).

The interaction radiation filtered by the second optical filter FO2 arrives at a second fluorescence detector DF2 where it is converted by photodetectors into electrical signals transmitted to a second fluorescence decoder (or demodulator) DRF2 of the analysis module MA that is responsible for demodulating them according to the first and second modulation frequencies ω1 and ω2 in order to deliver the signal PM2(ω1) and the signal PM2(ω2).

The fluorescence demodulators DRF1 and DRF2 are for example configured in the form of analog filtering stages, of the Butterworth bandpass type, centered on the modulation frequencies.

Under the aforementioned excitation conditions, the quantities of fluorochromes (or molar concentrations) Q1 and Q2 can be calculated using equations A5 and A6, whose coefficients $c_{11}$ and $d_{22}$ are defined by A2 and A3.

The molar concentration Q2 may be extracted from the fluorescence signal PM2, delivered by the second fluorescence detector DF2, by the second demodulator DRF2 using a filter of the bandpass type centered on the frequency ω2. Indeed, as indicated previously, owing to the optical crosstalk between fluorochromes, PM2 comprises two frequency components, PM2(ω2), which corresponds to the r.m.s. value or the peak-to-peak value of the electrical pulse filtered around the frequency ω2, and PM2(ω1), which corresponds to the optical crosstalk. Therefore, PM2=PM2(ω1)+PM2(ω2). These frequency components PM2(ω1) and PM2(ω2), which are defined by equations A15 and A16 in the Appendix, can be separated by means of a simple bandpass filter centered on the frequency ω2.

The molar concentration Q1 can be directly extracted from the fluorescence signal PM1 which is equal to PM1(ω1).

In a configuration that does not comprise a separation means LS, and which corresponds to the situations in which $\kappa_{12}=1$, the signals delivered by the sole fluorescence detector PM are given by equation A19 that may be reformulated in the form of equation A20 in the Appendix. The signals PM(ω1) and PM(ω2), which are given by equations A21 and A22 in the Appendix, may be extracted from the signal PM by demodulation.

Equation A21 enables Q2 to be calculated, and inserting Q2 into the equation A22 allows Q1 to be determined.

The example described hereinabove may be extended to any number of fluorochromes with a level of optical crosstalk of any given complexity.

In a second exemplary application, the analyzing device DA, according to the invention, allows the refractive index of the cells contained in a whole blood sample to be measured. In the case of cells of the erythrocytic strain, this refractive index is recognized as being representative of the concentration in corpuscular hemoglobin.

Indeed, from an optical point of view, the red blood cell is composed of a "lipid bilayer" membrane of around 7 nm in thickness and of refractive index close to 1.46. The intracellular content contains several solid compounds dissolved in aqueous phase, of which there are hemoglobin (~34 g/dl), salts (~0.7 g/dl) and a minority of organic compounds (~0.2 g/dl).

The refractive index may be written in the form given by equation A23.

The concentration (in mmol/dl) can be equated to a mass concentration (g/dl) since the molar mass of hemoglobin is known (M=66 500 g/mol). The average mass of hemoglobin dissolved in the red blood cell is 12 pg. This leads to an average concentration of 33 g/dl, or 5 mmol/l.

On whole blood, the hemoglobin measurement must be corrected by the hematocrit factor which is situated between around 40% and 55% for men, and around 35% and 45% for women. This hematocrit factor is taken to be equal to 0.42 (average value); for example, an average concentration of corpuscular hemoglobin of 5 mmol/l yields an average concentration of whole hemoglobin of 2.1 mmol/l for a measurement made on whole blood.

In view of the above and of equation A23, the refractive index of a red blood cell may be written:

$n(980\ nm)=1.34+0.0019*Hb$ (corpuscular concentration g/dl), for an analyzing wavelength of 980 nm, and $n(488\ nm)=1.35+0.0016*Hb$ (corpuscular concentration g/dl), for an analyzing wavelength of 488 nm.

The range of validity of these formulas will be taken for a corpuscular hemoglobin concentration (in g/dl) going from 25 to 50 g/dl.

The imaginary part of the refractive index at the analyzing wavelengths equal to 980 nm and 488 nm may be numerically determined by means of the following equations:

$\kappa(980\ nm)=1.47*10^{-5}*Hb$, and $\kappa(488\ nm)=3.7.10^{-5}*Hb$.

The corpuscular hemoglobin concentration may be determined using the measurement of the extinction coefficient at two wavelengths. For this purpose, the geometrical approach developed by A. G. Borovoi may be used, which enables the scattering cross section $C_{ext}$ of a spherically-approximated red blood cell to be calculated, whose expression is given by equation A24 in the Appendix.

Figure 6:
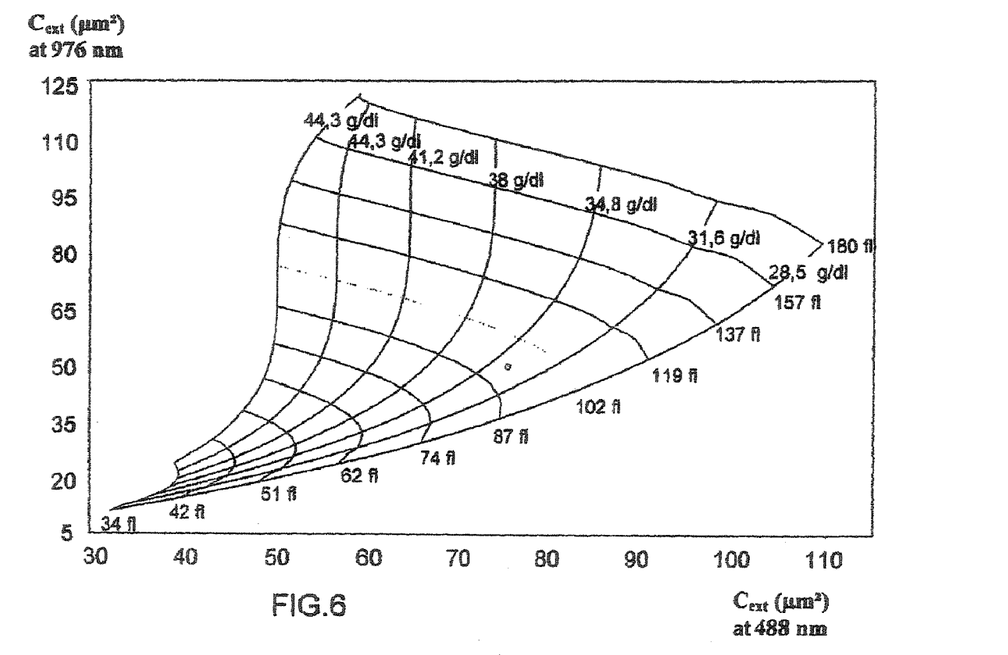
FIG. 6 is a diagram of isovolume and isoconcentration curves allowing the volume and the concentration of corpuscular hemoglobin to be determined as a function of the scattering cross sections $C_{ext}$ at the analyzing wavelengths equal to 488 nm and 976 nm.

A diagram of the isovolume and isoconcentration curves can be constructed, of the type of that illustrated in FIG. 6, allowing the volume and the concentration of corpuscular hemoglobin to be determined as a function of the scattering cross sections $C_{ext}$ at the analyzing wavelengths (here, 488 mm and 976 nm). In this diagram, to each pair of measurements $C_{ext}(488\ nm)$ and $C_{ext}(976\ nm)$ there corresponds a single sphere of given hemoglobin concentration and volume.

Obtaining the hemoglobin content and its monitoring can turn out to be particularly useful. This is notably the case for monitoring anemia and iron deficiencies. The average corpuscular hemoglobin load is indeed particularly useful to monitor during high medullary demands that are induced by growth hormone treatments ("r-Hu EPO therapy"). Monitoring of the reticulocytes and of their hemoglobin content in cellular therapy can also turn out to be useful, as indicated in the document by Carlo Brugnara "Iron Deficiency and Erythropoiesis: New Diagnostic Approaches", Clinical Chemistry 49: 10, 2003, pp. 1573-1578.

Thanks to the invention, it is now possible to carry out simultaneous hemoglobin content measurements (via scattering measurements) and other measurements (via fluorescence measurements), without interference between them, and with a reduced risk of error owing to the mode of processing.

In this case, the hemoglobin content may be advantageously completed by a fluorescence measurement of the intra-erythrocytic RNA allowing the young erythrocytes, or reticulocytes, to be isolated from the mature elements. One or more fluorescence wavelengths may be used simultaneously for additional markings enabling other potentially useful specific identifications, such as the identification of or the testing for:

red blood cells containing fetal hemoglobin (HbF), or red blood cells infested with a malaria parasite, or transferine (CD71) receptors, or the expression of glycophorine A (CD235a), as is notably described in the article by Hans J. Tanke "Reticulocytes and Mature Erythrocytes", Flow Cytometry in Hematology, ISBN 0-12-432940-3.

The applications of the invention are numerous both on nucleated cells (leucocytes and others) and on the erythroid strain or the thrombocytic elements (marking of the activation or platelet immaturity).

Furthermore, the invention is not only useful in the case of elements present in the blood or in the bone marrow, but can also be adapted to any biological cellular suspension, whether it be eukaryotic or prokaryotic.

In the description hereinabove, the invention has principally been described in the form of an analyzing device. However, the invention may also be considered in the form of an analytical method that can be implemented by the analyzing device described, and also by its variants.

Applications of the method, aside from flow cytometry, may be envisioned for in vivo or in vitro uses. For example, this method can be adapted to a device effecting the scanning of a cellular surface region (notably, smear test and tissue sectioning), or of a cellular suspension.

The invention is not limited to the optical analyzing device and method embodiments described hereinabove, by way of example only, but it encompasses all the variants that could be envisioned by those skilled in the art within the scope of the claims listed hereinbelow.

APPENDIX $$I_i(t) = \frac{I_{i0}(1 + M_i \cos(2\pi \omega_i t))}{2} \quad (A1)$$

where i=1 to n, $I_{io}$ is the maximum intensity of the radiation Ri, $M_i$ is the modulation depth (or the amplitude) (generally in the range between 0 and 1), $\omega i$ is the frequency of the modulation applied to the radiation Ri, and t is the time.

$$\begin{array}{lll} c_{11} = \alpha_{11}\eta_{11}F_{11} & c_{12} = 0 & c_{13} = 0 \\ c_{21} = \alpha_{11}\eta_{11}F_{12} & c_{22} = \alpha_{21}\eta_{21}F_{22} & c_{23} = 0 \\ c_{31} = \alpha_{11}\eta_{11}F_{13} & c_{32} = \alpha_{21}\eta_{21}F_{32} & c_{33} = \alpha_{31}\eta_{31}F_{33} \end{array} \quad (A2)$$

$$\begin{array}{lll} d_{11} = 0 & d_{12} = 0 & d_{13} = 0 \\ d_{21} = 0 & d_{22} = \alpha_{22}\eta_{22}F_{22} & d_{23} = 0 \\ d_{31} = 0 & d_{32} = \alpha_{22}\eta_{22}F_{32} & d_{33} = \alpha_{32}\eta_{32}F_{33} \end{array} \quad (A3)$$

$$\begin{array}{lll} e_{11} = 0 & e_{12} = 0 & e_{13} = 0 \\ e_{21} = 0 & e_{22} = 0 & e_{23} = 0 \\ e_{31} = 0 & e_{32} = 0 & e_{33} = \alpha_{33}\eta_{33}F_{33} \end{array} \quad (A4)$$

where $\alpha_{ij}$ is the molar absorption coefficient of the compound i at the wavelength $\lambda j$, $\eta_{ij}$ is the fluorescence efficiency of the compound i in the detection band Bj, $F_{ij}$ is the weighting factor in the range between 0 and 1 which relates to the fact that only a part of the fluorescence spectrum of the compound i is filtered within the detection band Bj.

$$Q_1 = c_{11} PM1(\omega_1) \quad (A5)$$

$$Q_2 = d_{22} PM2(\omega_2) \quad (A6)$$

$$Q_3 = e_{33} PM3(\omega_3) \quad (A7)$$

$$PM1 = \kappa_{12} * \kappa_{13} * PM_{10} \quad (A8)$$

$$PM2 = \kappa_{23} * PM_{20} + \rho_{12}(1-\kappa_{12})\kappa_{13} PM_{10} \quad (A9)$$

$$PM3 = PM_{30} + \rho_{13}(1-\kappa_{13})\kappa_{13} PM_{10} + \rho_{23}(1-\kappa_{23})PM_{10} \quad (A10)$$

where $\kappa_{ij}$ is a constant phenomenological coupling coefficient, in the range between 0 and 1, that represents the transfer of energy from a fluorochrome i toward a fluorochrome j, and $\rho_{ij}$ is a coefficient representing the quantum efficiency with which the light transferred, coming from the fluorochrome i, is converted into fluorescence light by the fluorochrome j.

$$PM1 = \kappa_{12} * PM_{10} \quad (A11)$$

$$PM2 = PM_{20} + \rho_{12}(1-\kappa_{12}) PM_{10} \quad (12)$$

$$PM3 = PM_{30} \quad (A13)$$

$$PM1(\omega 1) = \kappa_{12} \alpha_{11} \eta_{11} I_1 F_{11} Q_1 \quad (A14)$$

$$PM2(\omega 2) = \alpha_{22} \eta_{22} I_2 F_{22} Q_2 \quad (A15)$$

$$PM2(\omega 1) = \alpha_{21}\eta_{21}I_1 F_{22} Q_2 + \alpha_{11}\eta_{11}I_1 F_{12} Q_1 + \rho_{12}(1-\kappa_{12})\alpha_{11}\eta_{11}I_1 F_{11} Q_1 \quad (A16)$$

$$\kappa_{12} = \frac{PM1(\omega 1)\left[\rho_{12} + \frac{F_{12}}{F_{11}}\right]}{PM2(\omega 1) + \frac{\alpha_{21}\eta_{21}I_1}{\alpha_{22}\eta_{22}I_2} PM2(\omega 2) + \rho_{12} PM1(\omega 1)} \quad (A17)$$

$$Q_1 = (1/\kappa_{12} c_{11} I_1) PM1(\omega 1) \quad (A18)$$

$$PM = \left\{\frac{1}{a_{11}} - \left(\frac{a_{21}}{a_{12} a_{22}}\right)\right\} PM_{01} + \left(\frac{1}{a_{22}}\right) PM_{02} \quad (A19)$$

$$PM = (a_{11} + a_{21}) Q_1 + a_{22} Q_2 \quad (A20)$$

$$PM(\omega_2) = \alpha_{22}\eta_{22} I_2 F_{22} Q_2 \quad (A21)$$

$$PM(\omega_1) = \alpha_{21}\eta_{21} I_1 F_{22} Q_2 + \alpha_{11}\eta_{11} I_1 (F_{11} + F_{12}) Q_1 \quad (A22)$$

$$m(Hb,\lambda) = n(Hb,\lambda) - i\kappa(Hb,\lambda) \quad (A23)$$

where $n(HB,\lambda) = n_o(\lambda) + \alpha(\lambda) * Hb$ is the real part of the refractive index, $n_o(\lambda)$ is the refractive index of the pure solvent, being a function of the wavelength, $\alpha(\lambda)$ is the incremental coefficient of the refractive index characteristic of the hemoglobin and a function of the wavelength $\kappa(HB,\lambda)=\beta(\lambda)*Hb$ is the imaginary part of the refractive index, and $\beta(\lambda)$ is the molar absorption coefficient.

$$C_{ext}=\pi a^2 Q_{ext} \tag{A24}$$

with $$Q_{ext} = 2 - 4e^{-\rho\tan\beta}\frac{\cos\beta}{\rho}\sin(\rho-\beta) -$$
$$4e^{-\rho\tan\beta}\left(\frac{\cos\beta}{\rho}\right)^2 \cos(\rho-2\beta) + 4\left(\frac{\cos\beta}{\rho}\right)\cos(2\beta),$$

m=n−ik: complex refractive index of the red blood cell,
ρ=2x(n−1): parameter giving the phase difference,
x=2πa/λ,
a: radius of the sphere, and
tan β=κ/(n−1).

The invention claimed is:

1. A device for analyzing microscopic elements, the device comprising:
   a measurement space configured to analyze microscopic elements;
   at least one source configured to deliver analyzing radiation having at least two different analyzing wavelengths and to interact with said microscopic elements within said measurement space to form interaction radiation;
   fluorescent detection means for transforming at least a part of fluorescent interaction radiation originating from said measurement space into electrical signals;
   scattering detection means for transforming at least a part of scattering interaction radiation originating from said measurement space into electrical signals;
   analysis means for analyzing said electrical signals to allow data representative of said analyzed microscopic elements to be determined, the analysis means including decoding means for decoding said electrical signals to be analyzed as a function of code of origin;
   coding means for encoding said analyzing radiation upstream of said measurement space with different codes; and
   optical filtering means for selectively filtering any one of fluorescence interaction radiation and scattering interaction radiation as a function of wavelength, upstream of said detection means,
   wherein said coded analyzing radiation is conjugated within said measurement space.

2. The device as claimed in claim 1, wherein said at least one source sequentially applies analyzing radiation to said microscopic elements.

3. The device as claimed in claim 1, wherein said at least one source simultaneously applies analyzing radiation to said microscopic elements.

4. The device as claimed in one of claims 1 to 3, wherein said optical filtering means selectively filter said fluorescence interaction radiation whose having wavelengths in fluorescence analysis bands inserted between two analyzing wavelengths and placed beyond a longest analyzing wavelength.

5. The device as claimed in claim 1, wherein said at least one source includes at least two lasers configured to deliver conjugated radiation to said measurement space.

6. The device as claimed in claim 5, wherein said at least two lasers are of the monochrome type.

7. The device as claimed in claim 1, wherein said at least one source includes at least one light-emitting diode.

8. The device as claimed in claim 1, wherein said at least one source includes a source of polychromatic radiation.

9. The device as claimed in claim 8, wherein said source of polychromatic radiation is selected from a group consisting of at least one polychromatic laser with a substantially continuous spectrum, an incandescent lamp and an arc lamp.

10. The device as claimed in claim 1, wherein said at least one source delivers said analyzing radiation according to any one of a continuous mode and a pulsed mode.

11. The device as claimed in claim 1, wherein an intensity of each analyzing radiation beam delivered by said at least one source is adjustable.

12. The device as claimed in one claim 1, wherein said coding means modulate said analyzing radiation in intensity.

13. The device as claimed in claim 1, wherein at least a part of said coding means acts on the radiation downstream of said at least one source to form said analyzing radiation.

14. The device as claimed in claim 1, wherein at least a part of said coding means acts on said at least one source upstream of a distribution output for the analyzing radiation.

15. The device as claimed in claim 14, wherein at least a part of the coding means is integrated into said at least one source.

16. The device as claimed in claim 1, wherein said coding means include an acoustooptic modulator configured to modulate said radiation delivered by said at least one source to form said analyzing radiation.

17. The device as claimed in claim 1, wherein said fluorescent detection means and said scattering detection means include a multiplicity of photosensitive sensors to detect interaction radiation.

18. The device as claimed in claim 1, wherein said fluorescent detection means and said scattering detection means include a multiplicity of photosensitive sensors to detect interaction radiation, the multiplicity of photosensitive sensors being implanted in a location defined by an axis intercepting a general direction of propagation of the analyzing radiation at an obligatory passage, this axis being oriented at an angle in a range from 0° to 360° with respect to the general direction.

19. The device as claimed in claim 1, further including a computer system with a control software interface.

20. A method for analyzing microscopic elements, the method comprising:
   illuminating, from at least one source, microscopic elements within a measurement space with analyzing radiation conjugated within said measurement space to form interaction radiation, the analyzing radiation having at least two different analyzing wavelengths and codings according to different chosen codes;
   separating and selectively filtering, at an optical filter, any one of fluorescence interaction radiation and scattering interaction radiation as a function of wavelength;
   detecting and transforming, at a fluorescent detection unit, filtered fluorescence interaction radiation into electrical signals;
   detecting and transforming, at a scattering detection unit, filtered scattering interaction radiation into electrical signals; and
   decoding, at a decoder, the electrical signals as a function of code of origin to allow data representative of said analyzed microscopic elements to be determined.

21. The method as claimed in claim 20, wherein said analyzing radiation is applied sequentially to said microscopic elements to be analyzed.

22. The method as claimed in claim 20, wherein said analyzing radiation is applied simultaneously to said microscopic elements.

23. The method as claimed in one of claims 20 to 22, wherein said interaction radiation, whose wavelengths belong to fluorescence analysis bands inserted between two analyzing wavelengths and placed beyond a longest analyzing wavelength, is selectively filtered.

24. The method as claimed in claim 20 wherein a refractive index of one type of microscopic elements analyzed is deduced from signals resulting from transformation of the interaction radiation representative of a scattering process.

25. The method as claimed in claim 20 wherein in a presence of a sample of whole blood, a corpuscular hemoglobin concentration of cells of a erythrocytic strain is determined from said refractive index.

26. The method as claimed in claim 20 wherein a degree of coupling representative of a transfer of energy between fluorochromes is deduced from signals resulting from interaction between said analyzing radiation and two different, spatially close, fluorochromes.

27. A method for analyzing microscopic elements in a field of biological, biochemical, chemical, particulate, morphological analysis, multiparameter flow cytometry, the analysis of charged particles in a liquid or gaseous fluid, or particle size distribution, the method comprising:

illuminating, from at least one source, microscopic elements within a measurement space with analyzing radiation conjugated within said measurement space to form interaction radiation, the analyzing radiation having at least two different analyzing wavelengths and codings according to different chosen codes;

separating and selectively filtering, at an optical filter, any one of fluorescence interaction radiation and scattering interaction radiation as a function of wavelength;

detecting and transforming, at a fluorescent detection unit, filtered fluorescence interaction radiation into electrical signals;

detecting and transforming, at a scattering detection unit, filtered scattering interaction radiation into electrical signals; and decoding, at a decoder, the electrical signals as a function of code of origin to allow data representative of said analyzed microscopic elements to be determined.

28. A device for analyzing microscopic elements, the device comprising:

a measurement space configured to analyze microscopic elements;

at least one source configured to deliver analyzing radiation having at least two different analyzing wavelengths and to interact with said microscopic elements within said measurement space to form interaction radiation;

a fluorescent detection unit configured to transform at least a part of the interaction radiation originating from said measurement space into electrical signals;

a scattering detection unit configured to transform at least a part of scattering interaction radiation originating from said measurement space into electrical signals;

an analysis unit configured to analyze said electrical signals to allow data representative of said analyzed microscopic elements to be determined, the analysis unit including a decoding unit configured to decode said electrical signals to be analyzed as a function of code of origin;

a coding unit configured to encode said analyzing radiation upstream of said measurement space with different codes; and optical filtering means configured to selectively filter any one of fluorescence and scattering interaction radiation as a function of wavelength, upstream of said detection means, wherein said coded analyzing radiation is conjugated within said measurement space.

* * * * *